United States Patent
Storm, Jr. et al.

(10) Patent No.: US 6,807,857 B2
(45) Date of Patent: Oct. 26, 2004

(54) METHOD AND APPARATUS FOR DETERMINING DENSITY OF A FLOWING FLUID

(75) Inventors: Bruce H. Storm, Jr., Houston, TX (US); Mark A. Proett, Missouri City, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 10/163,236

(22) Filed: Jun. 5, 2002

(65) Prior Publication Data

US 2003/0226395 A1 Dec. 11, 2003

(51) Int. Cl.[7] .............................................. G01N 9/26
(52) U.S. Cl. ....................................................... 73/438
(58) Field of Search ............................ 73/32 R, 438, 73/54.09

(56) References Cited

U.S. PATENT DOCUMENTS

| | | | | |
|---|---|---|---|---|
| 3,839,914 A | * | 10/1974 | Modisette et al. ............. 73/438 |
| 3,840,051 A | * | 10/1974 | Akashi et al. ................. 138/37 |
| 3,924,467 A | | 12/1975 | Takamura et al. ............. 73/213 |
| 4,745,807 A | | 5/1988 | O'Neill ......................... 73/434 |
| 5,591,922 A | * | 1/1997 | Segeral et al. ............. 73/861.04 |
| 5,834,659 A | * | 11/1998 | Ortiz et al. ............... 73/861.69 |
| 6,422,092 B1 | * | 7/2002 | Morrison et al. ......... 73/861.04 |
| 6,550,327 B1 | * | 4/2003 | Van Berk ..................... 73/438 |

FOREIGN PATENT DOCUMENTS

WO    WO 95/04869    * 2/1995

OTHER PUBLICATIONS

Paper titled "Flow Diagnosis and Production Evaluation in High Flowrate Oil–Water Producers Using Optical–Fibre Holdup Sensors," R. R. Jackson, C. Ayan and J. Wakefield, Society of Petroleum Engineers, Inc. (2001).

* cited by examiner

Primary Examiner—Helen C. Kwok
(74) Attorney, Agent, or Firm—John W. Wustenberg; William D. Hall

(57) ABSTRACT

The current invention provides a process and apparatus for determining the density of a flowing fluid without requiring knowledge of the fluid's rheological properties. The process of the current invention is capable of providing continuous "real time" analysis of fluid density. The apparatus of the current invention comprises at least two pressure assessment zones fitted with fluid pressure sensing points. Pressure sensing devices connected to the pressure sensing points provide the data necessary to enable the calculation of fluid density.

31 Claims, 5 Drawing Sheets

METHOD AND APPARATUS FOR DETERMINING DENSITY OF A FLOWING FLUID

BACKGROUND OF THE INVENTION

Production of hydrocarbons from a well requires many different steps as well as an assortment of tools and chemicals. Common chemicals include fracturing fluids, viscosity breakers and scale inhibiting compounds. Effective use of these fluids requires an understanding of their chemical and physical characteristics. Frequently, successful economic well completion requires an accurate and continuous determination of fluid density. In particular, "real time" knowledge of fluid density can significantly reduce completion costs.

Typical instruments for determining fluid density include gradiomanometers and nuclear fluid density type tools. Although adequate for the purpose, neither instrument completely meets industry's needs. Readings from gradiomanometers are affected by turbulence and otherwise subject to deviation. Nuclear fluid density tools use a chemical gamma-ray source positioned with respect to a gamma-ray detector. Fluid passing between the gamma-ray source and detector absorbs gamma-rays. Thus a high radiation count indicates a low fluid density, while a low count indicates high fluid density. Nuclear fluid density tools provide suitable results; however, the use of a radioactive source creates safety and environmental concerns. Therefore, the ability to accurately measure the density of a flowing fluid without turbulence induced error or the use of radioactive material would be beneficial to the well completion industry.

SUMMARY OF THE INVENTION

The current invention provides an apparatus for determining the density of a flowing fluid. The apparatus comprises two pressure assessment zones. Each pressure assessment zone carries at least one pair of pressure sensing points. Typically, the first pressure assessment zone has an angle of inclination ranging from about 10° to about 90° or from about −10° to about −90° from horizontal and the second pressure assessment zone preferably has an identical angle of inclination. Preferably, the pressure assessment zones carrying the pressures sensing points have identical interior diameters.

The present invention also provides an apparatus for continuously determining the density of a flowing fluid. The apparatus for continuously determining the density of a flowing fluid comprises two pressure assessment zones joined in fluid communication. Each pressure assessment zone carries at least one pair of pressure sensing points. Typically, the first pressure assessment zone has an angle of inclination from about 10° to about 90° or from about −10° to about −90° from horizontal and the second pressure assessment zone preferably has an identical angle of inclination. Preferably, the pressure assessment zones carrying pressures sensing points have identical interior diameters. The pressure assessment zones carrying the pressure sensing points may optionally contain fluid flow straighteners. The pressure sensing points either transmit fluid pressure to a pressure sensor or designate the attachment point for the pressure sensor. To generate continuous, real time results, the pressure sensor is linked to a central processing unit, such as a personal computer, capable of continuously calculating the density of the fluid passing through the pressure assessment zones.

Additionally, the current invention provides a method for determining the density of a flowing fluid. The method passes the fluid either upward or downward through a first pressure assessment zone and measures fluid pressure as it passes through the first pressure assessment zone. Subsequently, the method passes the fluid in the opposite direction through a second pressure assessment zone and measures fluid pressure as it passes through the second pressure assessment zone. The method then calculates fluid density based on the pressure readings obtained from each pressure assessment zone.

The current invention also provides another method for determining the density of a flowing fluid. The method initially passes the fluid through a first pressure assessment zone at an angle between about 10° and 90° or between about −10° and −90° from horizontal. Subsequently, the fluid passes through a second pressure assessment zone at an angle identical to the first pressure assessment zone; however, the fluid flows in the opposite direction through the second pressure assessment zone. The method determines fluid pressure in each pressure assessment zone and calculates the density of the fluid.

Further, the current invention provides yet another method for continuously calculating the density of a flowing fluid. The method initially passes the fluid through a first pressure assessment zone at an angle between about 10° and 90° or between about −10° and −90° from horizontal. Subsequently, the fluid passes through a second pressure assessment zone at an angle identical to the first pressure assessment zone; however, the fluid flows in the opposite direction through the second pressure assessment zone. Thus, if the fluid flows upward through the first pressure assessment zone, then it will flow downward through the second pressure assessment zone. The method continuously determines the pressure in each pressure assessment zone and communicates the pressure readings to a central processor or other device suitable for continuously calculating the density of the flowing fluid.

DETAILED DESCRIPTION OF THE INVENTION

I. Apparatus for Measuring Density of a Flowing Fluid

The current invention will be described with reference to the drawings where like identification numbers refer to like components in each Figure. The current invention provides a means for measuring the density of a flowing fluid. When linked to a computer, the current invention provides the means for continuously monitoring the density of a flowing fluid.

FIGS. 1–5 depict some of the alternate embodiments of the fluid density tool 10 of the current invention. As shown, tool 10 comprises five zones 50, 60, 70, 80 and 90. Tool 10 may comprise a single conduit formed to the desired configuration or each zone may be a separate conduit joined by any conventional means. Preferably all joints will be welded; however, other conventional joining mechanisms, such as bolting flanged joints, will work equally well. Regardless of the joining mechanism or use of a continuous conduit, the zones function in the same manner.

Figure 1:
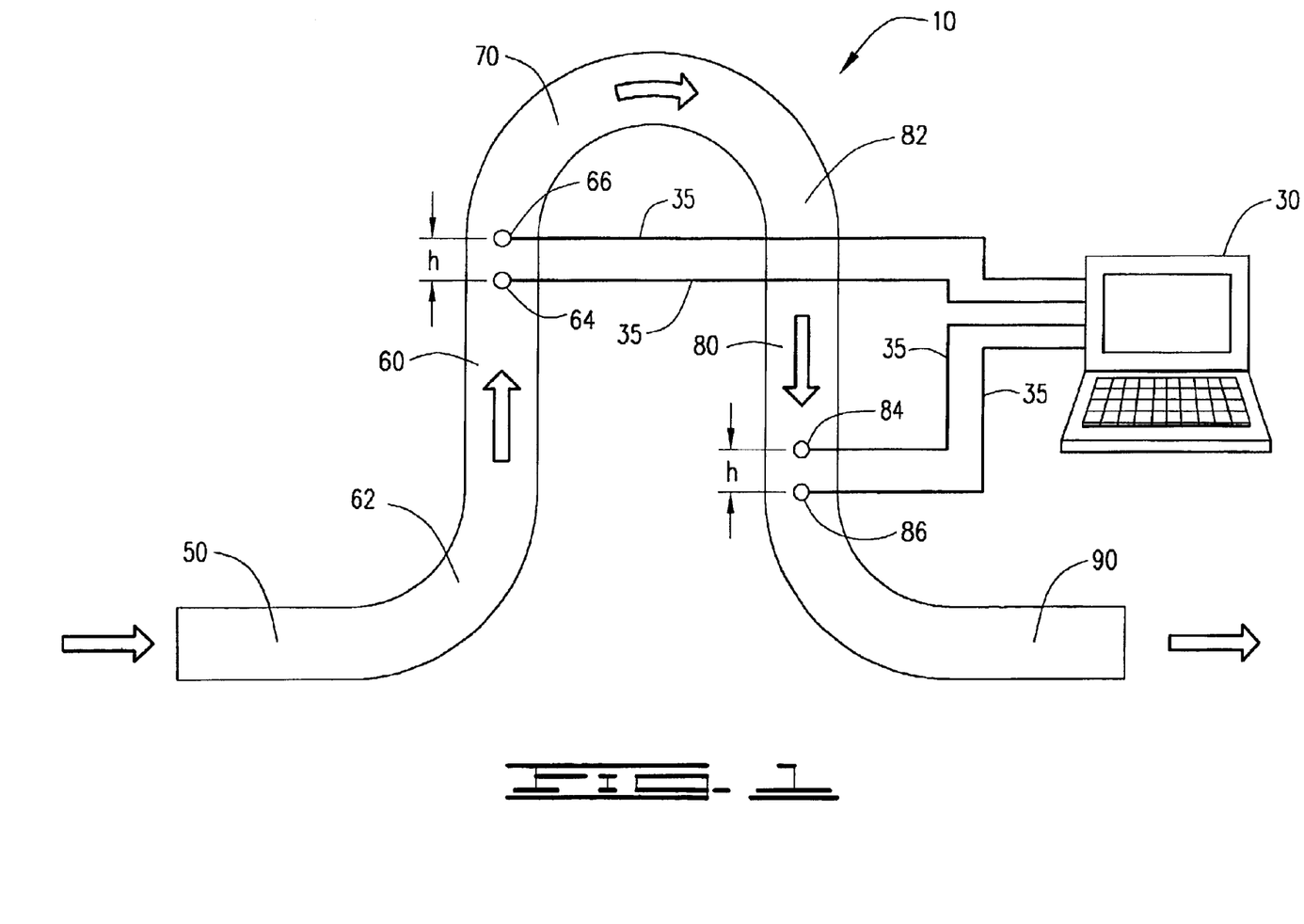
FIGS. 1–4 each depict the side view of several possible embodiments of the current invention.

In FIG. 1, zone 50 provides the entry port to tool 10; and also provides a smooth transition to pressure assessment zone 60. Pressure assessment zones 60 and 80 are joined by zone 70. In the embodiment of FIG. 1, the smooth continuous curve of zone 70 promotes the continuity of fully structured flow patterns in the fluid during transition from zone 60 to zone 80. Pressure sensing points 64, 66, 84 and 86 are located within each pressure assessment zone 60 and 80. Preferably, the distance, h, separating pressure sensing points 64 and 66 is identical to the distance separating pressure sensing points 84 and 86. Further, each pair of pressure sensing points, 64–66 and 84–86, are preferably positioned a sufficient distance from each entrance 62 and 82 to permit the development of structured flow regimes. A structured flow regime will preferably be fully developed in nature. However, the current invention will provide satisfactory results with turbulent flow provided that the turbulent flow in each pressure assessment zone is symmetrical in nature. Therefore, as used herein, the term "structured flow" indicates a fluid flow state substantially similar in each pressure assessment zone 60 and 80. Preferably, the structured flow will be identical in each pressure assessment zone. Typically, pressure sensing points 64–66 and 84–86 will be an identical distance from each entrance 62 and 82. If necessary for the generation of structured flow, a fluid flow straightener 68 may be placed in either or both pressure assessment zones 60 and 80. When placed a sufficient distance upstream from the pressure sensing points, fluid straightener 68 generates structured fluid flow over the pressure sensing points 64–66 and 84–86. Preferably, the flow will be fully developed as it passes over the pressure sensing points 64–66 and 84–86. Finally, zone 90 provides the exit to tool 10.

Fluid pressure readings are obtained at each pressure sensing point, 64, 66, 84 and 86. Pressure readings are obtained by conventional pressure sensors, not shown, such as strain gauges, quartz pressure gauges, and pressure sensors connected by conventional means to each pressure sensing point. Alternatively, a differential pressure sensor may be linked to a pair of pressure points, for example 64 and 66. The type of pressure sensing device is not critical to the current invention. To enable continuous analysis of fluid density, conventional data transmission lines 35 link the pressure sensors to a conventional calculating device 30 such as a personal computer.

Figure 2:
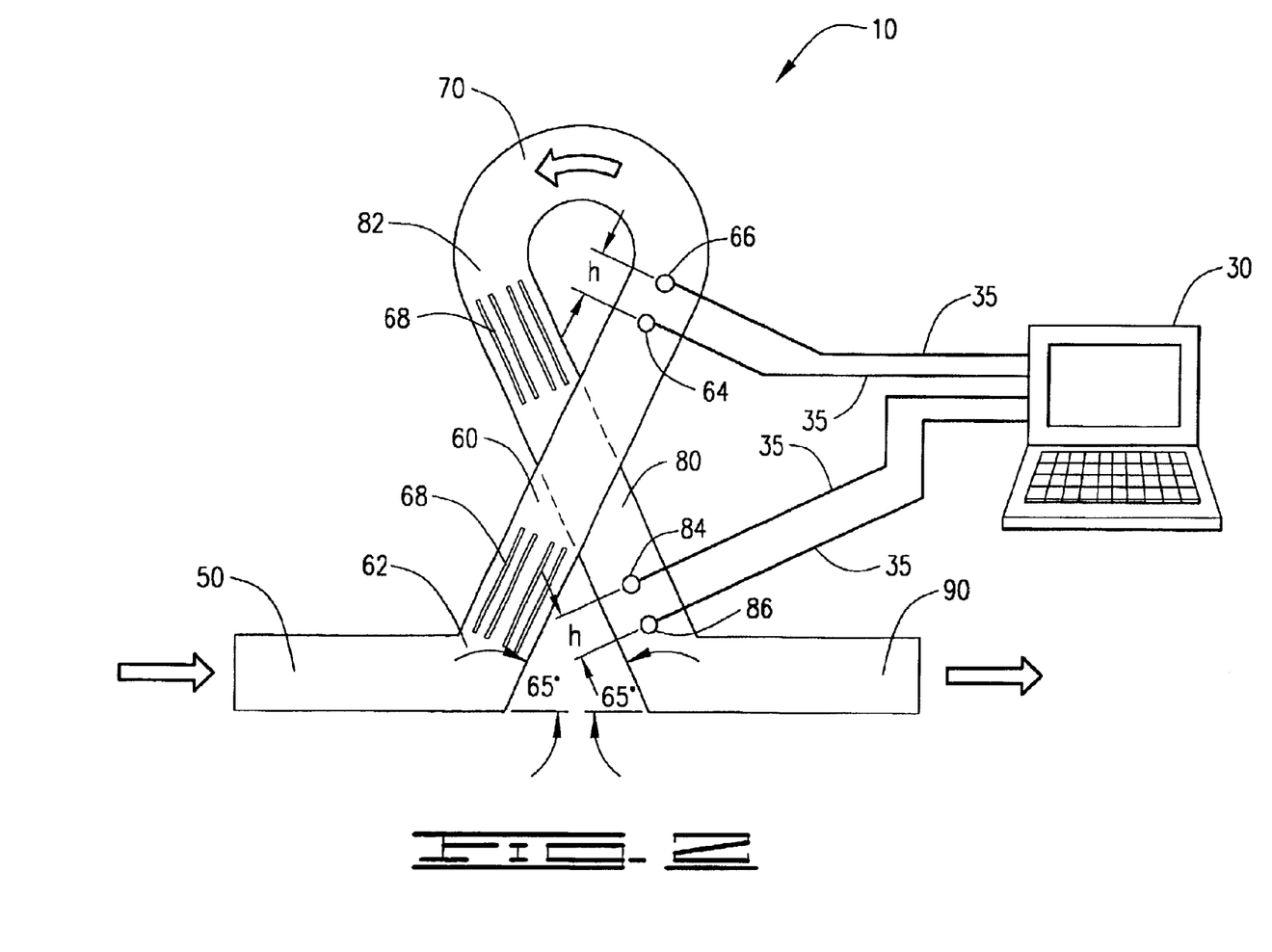
Figure 3:
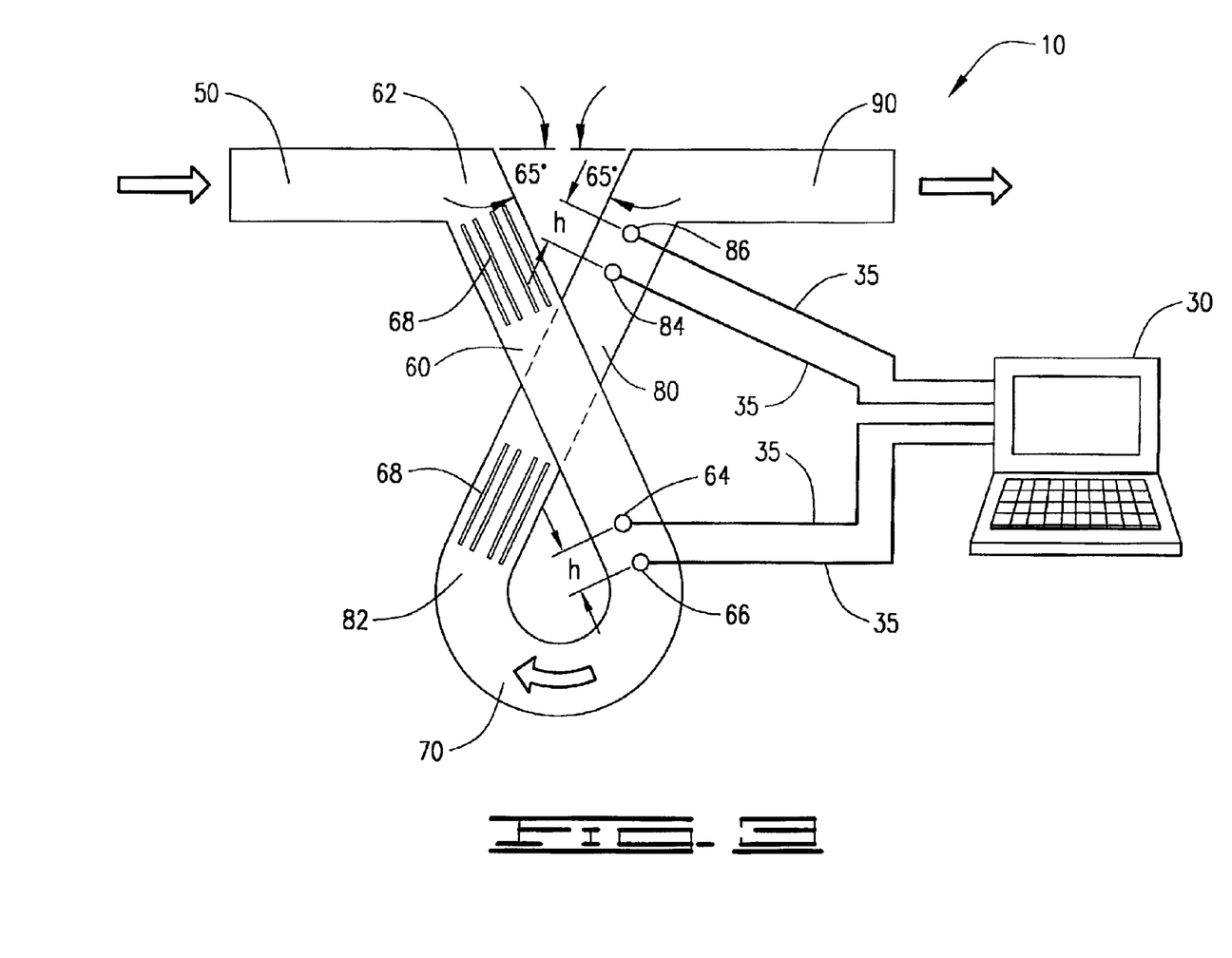

FIGS. 2 and 3 depict alternative embodiments of tool 10. These alternate embodiments may allow for placement of tool 10 in locations unsuitable for the embodiments depicted in FIGS. 1 and 3. The embodiment depicted in FIG. 2 has five zones corresponding to the zones of the embodiment depicted in FIG. 1. FIG. 2 demonstrates that tool 10 will work effectively when pressure assessment zones 60 and 80 have angles of inclination other than vertical. In general, the angle of inclination for pressure assessment zones 60 and 80 may range from about +10° to +90° or from about −10° to −90° from horizontal. Preferably, the angle of inclination for each pressure assessment zone will be identical thereby allowing the effects of viscous forces to cancel. Therefore, the fluid initially flows either upward or downward through pressure assessment zone 60 and subsequently flows in the opposite direction at an identical angle through pressure assessment zone 80.

FIG. 3 depicts an inverted tool 10. The ability to invert the tool without detrimentally impacting the process of using the tool may have several advantages in the field. Inverted tool 10 demonstrates the configuration of the current invention with angles of inclination ranging from about −10° to −90° from horizontal. The following section on the process of the current invention provides a detailed explanation of the functional aspects of the current invention.

Figure 4:
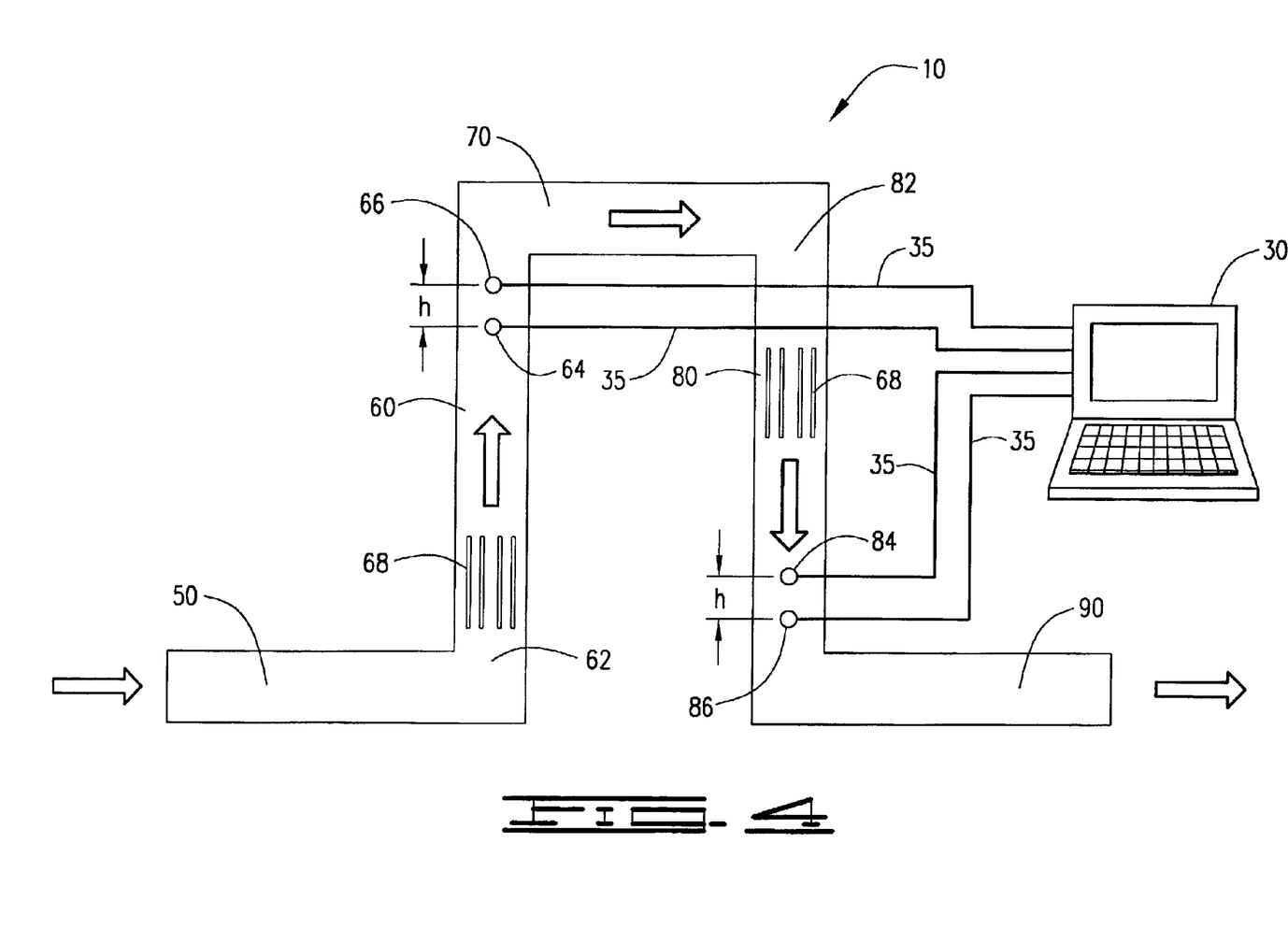

FIG. 4 depicts yet another embodiment of the current invention. This embodiment allows for construction of tool 10 from pipe or conduit readily available at the well site. As shown in FIG. 4, tool 10 has the same five zones as the embodiments of FIGS. 1, 2 and 3. However, the embodiment of FIG. 4 lacks the smooth transition from one zone to the next of the other embodiments. As a result of the abrupt change in fluid flow, this arrangement requires positioning of pressure sensing points 64, 66, 84 and 86 a greater distance from each entrance 62 and 82. The increased distance permits development of structured fluid flow. Alternatively, fluid flow straighteners 68 may be placed within pressure assessment zones 60 and 80. Fluid flow straighteners 68 reduce turbulence within the flowing fluid permitting rapid development of structured flow. Preferably, fluid flow straighteners 68 yield a fully developed flow as the fluid passes over pressure sensing points 64–66 and 84–86. Although FIG. 4 depicts pressure assessment zones 60 and 80 as vertical passages, these zones may have angles of inclination between about +10° to +90° or about −10° to −90° from horizontal as disclosed in FIGS. 2 and 3. As in the embodiments of FIGS. 2 and 3, the angle of inclination is preferably identical for each pressure assessment zone.

Figure 5A:
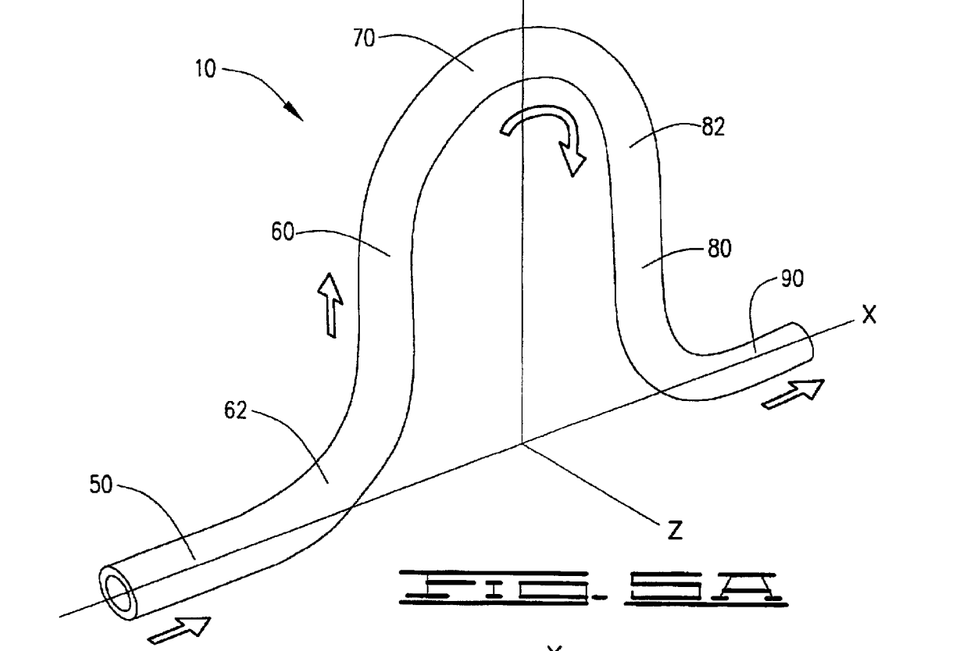
FIG. 5 depicts an end view of an alternative embodiment of the current invention.
Figure 5B:
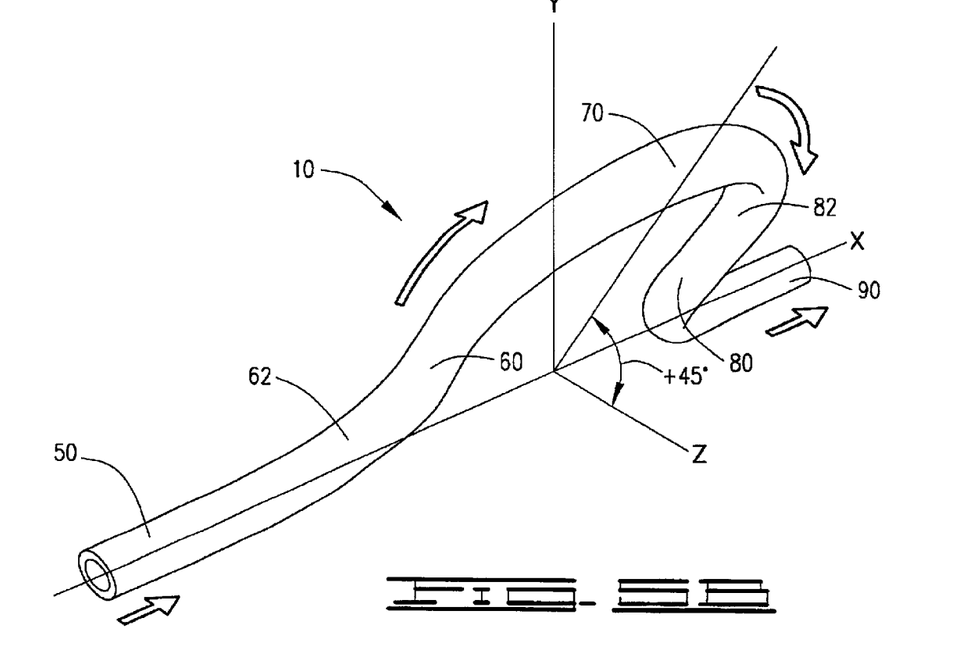

The embodiments of tool 10 depicted in FIGS. 1–4 are merely four variations of several embodiments suitable for the current invention. For example, the embodiments of FIGS. 1–4 depict each zone as having an identical internal diameter. However, only zones 60 and 80 must have identical internal diameters. Zones 50, 70 and 90 may vary in diameter. FIGS. 1–4 depict the invention in the x-y axis only. However, one skilled in the art will recognize that rotating the invention about the x-axis, as shown by comparing FIG. 5b to FIG. 5a, will not detrimentally impact the function of the invention. FIG. 5a shows fluid density tool 10 aligned vertically, i.e. +90° from horizontal, while FIG. 5b shows fluid density tool 10 rotated about the x-axis approximately +45° from horizontal. In general, rotation about the x-axis may range from +10° to +90° and from −10° to −90° from horizontal.

II. Process for Measuring Density of a Flowing Fluid

The current invention provides a process for measuring the density of a flowing fluid. The novel process does not require prior knowledge of the fluid's viscosity or the flow rate. Rather, the process utilizes differential pressure measurements performed as the fluid passes over pressure sensing points located on or within a pressure assessment zone. Linked to or fixed in the pressure sensing points are pressure sensing devices or gauges. The pressure sensing devices are preferably linked to a central processing unit, such as a personal computer, and provide the data necessary to permit calculation of fluid density. The following detailed explanation of the novel process will reference FIGS. 1–5.

As shown in the Figs., fluid passes through zone 50 into pressure assessment zone 60. Fluid passing through pressure assessment zone 60 contacts at least one pair of pressure sensing points 64 and 66. The fluid subsequently passes through zone 70 into pressure assessment zone 80 where it contacts at least one pair of pressure sensing points 84 and 86. Pressure sensing points 64 and 66 and pressure sensing points 84 and 86 are preferably located identical distances from the entrances 62 and 82 respectively. However, the only limiting requirement on the location of the pressure sensing points in each pressure assessment zone is the need for structured fluid flow over each pair of pressure sensing points. As the fluid passes over pressure sensing points 64 and 66, pressure readings are performed by pressure sensing devices, not shown. Conventional pressure sensing devices, as described above, are suitable for use in the current invention. The various pressure sensing devices suitable for use in the current invention and methods for using the same are well known to those skilled in the art.

Pressure readings obtained by the pressure sensing devices are preferably transmitted to a central processing unit 30, such as a personal computer, over electrical, infrared, fiber optic or other conventional data transmission means 35. Processing unit 30 interprets the data obtained from each pressure sensing device and provides the means for instantaneously and continuously calculating and reporting the fluid density. If continuous, instantaneous readings are not necessary, then the operator may receive the pressure readings on a suitable display (not shown) and manually calculate the fluid density.

The configuration of pressure assessment zones 60 and 80 permits continuous real time calculation of fluid density due to the cancellation of forces acting on the flowing fluid. The cancellation of forces allows one to calculate the density or mass of the fluid present between pressure sensing device 64 and pressure sensing device 66 as well as the density or mass of fluid between pressure sensing points 84 and 86. Typically, density is the preferred calculation. Fluid density is determined by measuring the difference in pressure produced by the fluid column passing through pressure assessment zone 60 compared to the pressure produced as the fluid passes through pressure assessment zone 80.

For those configurations having vertical pressure assessment zones 60 and 80, the forces acting on the fluid in pressure assessment zone 60 are defined by the following equation:

$$\Sigma F = A(P_{64}-P_{66})\hat{i} - F_g\hat{j} - F_\mu\hat{j} = dp_u/dt$$

where A is the cross sectional area, $P_{64}$ and $P_{66}$ are the pressure readings at the respective pressure sensing points, $F_g$ and $F_\mu$ are the magnitudes of gravitational and viscosity dependent forces and p denotes the momentum vector. In pressure assessment zone 80, the forces acting on the fluid are defined by the following equation:

$$\Sigma F = -A(P_{84}-P_{86})\hat{i} - F_g\hat{j} + F_\mu\hat{j} = dp_d/dt$$

where $P_{84}$ and $P_{86}$ are the pressure readings at the respective pressure sensing points. If the fluid is a constant velocity, then both $dp_u/dt$ and $dp_d/dt$ equal zero. For FIGS. 1, 2 and 4, the effect of flowing the fluid at a downward angle identical to the upward angle of flow is revealed by a comparison of the two equations. Specifically, the component of Force due to fluid viscosity ($F_\mu\hat{i}$) in pressure assessment zone 80 is in the opposite direction of the same force in pressure assessment zone 60. Therefore, if the fluid has structured fluid flow and identical flow rates in each section, the magnitude of this force will be the same in pressure assessment zones 60 and 80. Accordingly, addition of the force equations yields the following equation:

$$A[(P_{64}-P_{66})-(P_{84}-P_{86})]\hat{i} = 2F_g\hat{j}.$$

From this equation, one skilled in the art will recognize that the pressure data obtained from pressure sensing points 64, 66, 84 and 86 provides the ability to calculate the density of the fluid contained in the area between pressure sensing points 64 and 66 and/or pressure sensing points 84 and 86. The following equation defines the calculation of the density (ρ) using the data from the pressure sensing points:

$$\rho = [(P_{64}-P_{66})-(P_{84}-P_{86})]/2gh.$$

As used in the equation, g is the acceleration due to gravity and h is the distance separating each pressure sensing point in the pressure sensing pairs 64–66 and 84–86. The density calculation can be performed manually or on a continuous, real time basis by central processing unit 30.

The foregoing discussion has described the flow of the fluid as first upward through pressure assessment zone 60 and subsequently downward through pressure assessment zone 80. However, the current invention will perform equally well whether the fluid first flows upward or first flows downward through pressure assessment zone 60. Therefore, tool 10 can easily be inverted, as depicted in FIG. 3, without impacting the performance of tool 10 or the process steps of the current invention. Further, one skilled in the art will recognize that knowledge of the angle of inclination (if any) allows a similar resolution of force vectors into components parallel and perpendicular to the flow direction in zones 60 and 80. Thus, one may calculate fluid density without knowledge of the fluid's rheological properties.

The following examples describe the current invention with respect to turbulent and non-turbulent flow of a fluid passing through the embodiment of the current invention depicted in FIG. 1. As depicted, fluid will initially pass upward through zone 60 and subsequently downward through zone 80. For the purposes of these examples, the fluid is deemed to have the following properties:

Density (ρ)=1 g/cc

Viscosity ($\mu$)=10 cP

The dimensions of the apparatus of the current invention are:

Diameter (d)=10 cm

Distance between pressure sensing points for each pair of pressure sensing points=h=1 meter Acceleration due to gravity, g, is 9.8 m/s².

Non-Turbulent Flow

In this example, the fluid would pass through the apparatus of the current invention in a manner substantially free of turbulence. In this example, the average fluid velocity (V) is considered to be 10 cm/s. The associated Reynold's number for structured flow would be 1000.

In pressure assessment zone 60, the pressure difference ($P_{64}-P_{66}$) would be 9,803.2 Pa. In pressure assessment zone 80, the pressure difference ($P_{84}-P_{86}$) would be −9,796.8 Pa. Taking the difference between these measured pressures and dividing the result by 2·g·h yields a density measurement of 1×10³ kg/m³ (1 g/cc) as shown by the equation below.

$$\frac{(P_{64}-P_{66})-(P_{84}-P_{86})}{2\cdot g\cdot h} = \frac{(9,803.2-(-9796.8))}{2\cdot 9.8\cdot 1} = 1\times 10^3 \frac{kg}{m^3}$$

Turbulent Flow

In this example, no effort would be made to reduce turbulence within the pressure assessment zones 60 and 80; however, the flow through each zone would be structured flow as defined above.

In this example, the average fluid velocity (V) is considered to be 100 cm/s. The associated Reynolds number for structured flow would be 10,000. In pressure assessment zone 60, the pressure difference ($P_{64}-P_{66}$) would be 9,958 Pa. In pressure assessment zone 80, the pressure difference ($P_{84}-P_{86}$) would be −9,642 Pa. Taking the difference between these measured pressures and dividing the result by 2·g·h yields a density of 1×10³ kg/m³ (1 g/cc) as shown by the equation below.

$$\frac{(P_{64} - P_{66}) - (P_{84} - P_{86})}{2 \cdot g \cdot h} = \frac{(9,958 - (-9,642))}{2 \cdot 9.8 \cdot 1} = 1 \times 10^3 \frac{kg}{m^3}$$

While the present invention has been described with reference to FIGS. 1–5, other embodiments of the current invention will be apparent to those skilled in the art. Therefore, the foregoing specification is considered exemplary with the true scope and spirit of the invention being indicated by the following claims.

We claim:

1. A method for determining the density of a flowing fluid comprising the steps of:
   a) passing a fluid upwards or downwards through a first pressure assessment zone;
   b) measuring the pressure of the fluid as it passes over at least one pair of pressure sensing points in the first pressure assessment zone, the pressure sensing points being placed a distance apart;
   c) passing the fluid through a second pressure assessment zone the fluid flow direction through the second pressure assessment zone is in the opposite direction of that used in step a);
   d) measuring the pressure of the fluid as it passes over at least one pair of pressure sensing points in the second pressure assessment zone, the pressure sensing points being placed a distance apart and wherein the fluid passing over the pressure sensing points in the first and second pressure assessment zones has structured fluid flow; and,
   e) using pressure readings from the first and second pressure assessment zones to calculate the density of the fluid.

2. The method of claim 1, wherein the fluid flows through the first pressure assessment zone at an angle between about 10° and 90° or an angle between about −10° and −90° and flows through the second pressure assessment zone at an identical angle.

3. The method of claim 1, wherein the fluid flows an equal distance through the first and second pressure assessment zones prior to passing over the pressure sensing points in the first and second pressure assessment zones.

4. The method of claim 1, wherein the step of calculating density is performed continuously.

5. The method of claim 1, further comprising the steps of passing the fluid through a flow straightener positioned within each pressure assessment zone prior to carrying out steps b) and d).

6. A method for determining the density of a flowing fluid comprising the steps of:
   a) passing a fluid upward or downward at an angle between about 10° and 90° or about −10° to −90° from horizontal through a first pressure assessment zone;
   b) measuring the pressure of the fluid as it passes over at least one pair of pressure sensing points in the first pressure assessment zone, the pressure sensing points being placed a distance apart;
   c) passing the fluid through a second pressure assessment zone, the second pressure assessment zone having an angle equal to the angle of the first pressure assessment zone, the fluid flow direction through the second pressure assessment zone is in the opposite direction of that used in step a);
   d) measuring the pressure of the fluid as it passes over at least one pair of pressure sensing points in the second pressure assessment zone, the pressure sensing points being placed a distance apart and wherein the fluid passing over the pressure sensing points in the first and second pressure assessment zones has structured fluid flow; and,
   e) using pressure readings from the first and second pressure assessment zones to calculate the density of the fluid.

7. The method of claim 6, wherein the fluid flows through the first and second pressure assessment zones a distance sufficient to generate structured fluid flow prior to passing over the pressure sensing points in the pressure assessment zones.

8. The method of claim 6, further comprising the steps of passing the fluid through a flow straightener positioned within each pressure assessment zone prior to carrying out steps b) and d).

9. A method for continuously calculating the density of a flowing fluid comprising the steps of:
   a) passing a fluid upward or downward at an angle between about 10° and 90° or between about −10° to −90° from horizontal through a first pressure assessment zone;
   b) measuring the pressure of the fluid as it passes over at least one pair of pressure sensing points in the first pressure assessment zone, the pressure sensing points being placed a distance apart;
   c) passing the fluid through a second pressure assessment zone at an angle equal to the angle of the first pressure assessment zone, the fluid flow direction through the second pressure assessment zone is in the opposite direction of that in step a);
   d) measuring the pressure of the fluid as it passes over at least one pair of pressure sensing points in the second pressure assessment zone, the pressure sensing points being placed a distance apart and wherein the fluid passing over the pressure sensing points in the first and second pressure assessment zones has structured fluid flow; and,
   e) using pressure readings from the first and second pressure assessment zones to continuously calculate the density of the fluid.

10. The method of claim 9, wherein the fluid flows vertically upward or downward through the first pressure assessment zone and flows vertically in the opposite direction through the second pressure assessment zone.

11. The method of claim 9, wherein the fluid flows through the first and second pressure assessment zones a distance sufficient to generate structured fluid flow prior to passing over the pressure sensing points.

12. The method of claim 9, further comprising the steps of passing the fluid through a flow straightener positioned within each pressure assessment zone prior to carrying out steps b) and d).

13. An apparatus for determining the density of a flowing fluid comprising:
   a first pressure assessment zone;
   a second pressure assessment zone;
   the first pressure assessment zone carries at least one pair of pressure sensing points;
   the second pressure assessment zone carries at least one pair of pressure sensing points, wherein the pressure sensing points in the first pressure assessment zone and the pressure sensing points in the second pressure assessment zone are an equal distance from the entrance of each pressure assessment zone; and, means for determining the density of the flowing fluid, said means for determining density being linked to each pair of pressure sensing points.

14. The apparatus of claim 13, wherein the first pressure assessment zone has an angle of inclination of about 10° to 90° or from about −10° to −90° from horizontal and the second pressure assessment zone has an identical angle of inclination.

15. The apparatus of claim 13, further comprising at least one pressure sensor connected to the pressure sensing points carried by the first pressure assessment zone and at least one pressure sensor connected to the pressure sensing points carried by the second pressure assessment zone.

16. The apparatus of claim 15, wherein said pressures sensor is a device selected from the group consisting of strain gauges, quartz pressure gauges, pressure sensors and differential pressure sensors.

17. The apparatus of claim 13, wherein the interior diameter of the first pressure assessment zone equals the interior diameter of the second pressure assessment zone.

18. The apparatus of claim 13, further comprising at least one flow straightener positioned within each pressure assessment zone.

19. The apparatus of claim 13, wherein the distance between the pressure sensing points in the first pressure assessment zone is identical to the distance between the pressure sensing points in the second pressure assessment zone.

20. An apparatus for determining the density of a flowing fluid comprising:

a first pressure assessment zone positioned at an angle of inclination of about 10° to 90° or of about −10° to −90° from horizontal;

a second pressure assessment zone positioned at an identical angle of inclination to the first pressure assessment zone;

the first pressure assessment zone and the second pressure assessment zone are joined in fluid communication;

the first pressure assessment zone carries at least one pair of pressure sensing points;

the second pressure assessment zone carries at least one pair of pressure sensing points, wherein the distance between each pressure sensing point in the first pressure assessment zone is identical to the distance between each pressure sensing point in the second pressure assessment zone and wherein the pressure sensing points in the first pressure assessment zone and the pressure sensing points in the second pressure assessment zone are placed an equal distance from the entrance of each pressure assessment zone; and, means for determining the density of the flowing fluid, said means for determining density being linked to each pair of pressure sensing points.

21. The apparatus of claim 20, further comprising at least one pressure sensor connected to the pressure sensing points carried by the first pressure assessment zone and at least one pressure sensor connected to the pressure sensing points carried by the second pressure assessment zone.

22. The apparatus of claim 21, wherein said pressures sensor is a device selected from the group consisting of strain gauges, quartz pressure gauges, pressure sensors and differential pressure sensors.

23. The apparatus of claim 20, further comprising at least one flow straightener positioned within each pressure assessment zone.

24. The apparatus of claim 20, wherein the interior diameter of the first pressure assessment zone equals the interior diameter of the second pressure assessment zone.

25. An apparatus for continuously determining the density of a flowing fluid comprising:

a first pressure assessment zone positioned at an angle of inclination of about 10° to 90° or of about −10° to −90° from horizontal;

a second pressure assessment zone positioned at an identical angle of inclination to the first pressure assessment zone;

the first pressure assessment zone and the second pressure assessment zone are in fluid communication;

the first pressure assessment zone carries at least one pair of pressure sensing points;

the second pressure assessment zone carries at least one pair of pressure sensing points;

the pair of pressure sensing points in the first pressure assessment zone and the pair of pressure sensing points in the second pressure assessment zone are positioned an identical distance from the entrance to each pressure assessment zone; and, means for continuously determining the density of the flowing fluid, said means for determining density being linked to each pair of pressure sensing points.

26. The apparatus of claim 25, wherein the means for continuously determining the density of the fluid is a personal computer.

27. The apparatus of claim 25, further comprising at least one pressure sensor connected to the pressure sensing points carried by the first pressure assessment zone and at least one pressure sensor connected to the pressure sensing points carried by the second pressure assessment zone.

28. The apparatus of claim 25, wherein said pressures sensor is a device selected from the group consisting of strain gauges, quartz pressure gauges, pressure sensors and differential pressure sensors.

29. The apparatus of claim 25, further comprising at least one flow straightener positioned within each pressure assessment zone.

30. The apparatus of claim 25, wherein the interior diameter of the first pressure assessment zone equals the interior diameter of the second pressure assessment zone.

31. The apparatus of claim 25, wherein the distance between the pressure sensing points in the first pressure assessment zone is identical to the distance between the pressure sensing points in the second pressure assessment zone.

* * * * *